United States Patent [19]
Hilliard, Jr. et al.

[11] Patent Number: 5,730,963
[45] Date of Patent: Mar. 24, 1998

[54] COSMETIC GEL COMPOSITION HAVING REDUCED SKIN IRRITATION

[75] Inventors: Peter R. Hilliard, Jr., Far Hills; Bhalchandra D. Moghe, White House Station; Lloyd Ross, Hampton, all of N.J.

[73] Assignee: Colgate-Palmolive Company, New York, N.Y.

[21] Appl. No.: 689,782

[22] Filed: Aug. 14, 1996

Related U.S. Application Data

[60] Provisional application No. 60/002,516, Aug. 18, 1995.

[51] Int. Cl.$^6$ ........................................ A61K 7/32
[52] U.S. Cl. ................ 424/65; 424/401; 424/66; 424/67; 424/68; 514/944
[58] Field of Search ................ 424/401, 65, 66, 424/67, 68; 514/944

[56] References Cited

U.S. PATENT DOCUMENTS

| | | |
|---|---|---|
| 4,322,400 | 3/1982 | Yuhas . |
| 4,382,079 | 5/1983 | Marschner . |
| 4,504,465 | 3/1985 | Sampson et al. . |
| 4,702,916 | 10/1987 | Geria . |
| 4,759,924 | 7/1988 | Luebbe et al. . |
| 4,904,466 | 2/1990 | Carson et al. ............... 424/763 |
| 4,956,174 | 9/1990 | Lang et al. ................. 424/63 |
| 5,114,717 | 5/1992 | Kuznitz et al. . |
| 5,128,123 | 7/1992 | Brewster et al. . |
| 5,200,174 | 4/1993 | Gardlik et al. ............... 424/66 |
| 5,284,649 | 2/1994 | Juneja . |
| 5,380,707 | 1/1995 | Barr et al. . |
| 5,424,070 | 6/1995 | Kasat et al. ................. 424/401 |
| 5,605,681 | 2/1997 | Trandai et al. ............... 424/65 |
| 5,609,855 | 3/1997 | Oh et al. ..................... 424/65 |

FOREIGN PATENT DOCUMENTS

| | | |
|---|---|---|
| 0107330A3 | 5/1984 | European Pat. Off. . |
| 0284765B1 | 10/1988 | European Pat. Off. . |
| 0404532A1 | 12/1990 | European Pat. Off. . |
| 0404533A1 | 12/1990 | European Pat. Off. . |
| 49148 A2 | 3/1991 | European Pat. Off. . |
| 512770 A1 | 11/1992 | European Pat. Off. . |
| 63-270614 | 8/1988 | Japan . |
| 2217594 | 11/1989 | United Kingdom . |
| WO91/04009 | 4/1991 | WIPO . |
| 92/05767 | 4/1992 | WIPO . |

OTHER PUBLICATIONS

Anonymous Research Disclosure No. 374 (Jun. 1995), p. 417.

*Primary Examiner*—Jyothsan Venkat
*Attorney, Agent, or Firm*—Richard J. Ancel; Rosemary M. Miano

[57] ABSTRACT

Disclosed is a glycol-containing base gel composition having reduced skin irritation potential, in which a cosmetically active agent (e.g., deodorant active agent, sunscreen, antiperspirant active agent, etc.) can be incorporated to provide a cosmetic gel (e.g., soft gel or stick) composition. The gelling agent for the gel composition can be a soap. The base gel composition includes at least one glycol having a structure of the formula $H(OC_3H_6)_nOH$, where n represents the number of repeating propylene oxide groups and ranges from 1–80, with the provisos that: (1) more than zero, and up to 100% by weight, of the glycol component, has n=3 or 4; (2) less than 20% by weight of the glycol component has n=1; (3) not more than 90% by weight of the glycol component has n=2; and (4) not more than 90% by weight of the glycol component has n greater than or equal to 5. The composition can further include a nonionic or anionic surface active agent as a clarifying agent, to provide a translucent or clear gel composition.

29 Claims, No Drawings

COSMETIC GEL COMPOSITION HAVING REDUCED SKIN IRRITATION

Priority is claimed under 35 USC 119 (e)(1) based on Provisional application Ser. No. 60/002,516, filed Aug. 18, 1995 now abandoned.

BACKGROUND OF THE INVENTION

The present invention is directed to a cosmetic gel composition containing a glycol (or mixture of glycols) and having reduced skin irritation potential. More specifically, the present invention is directed to a cosmetic soft gel or solid stick composition containing a glycol (or mixture of glycols) and having reduced skin irritation potential. The present invention has particular use in, e.g., deodorant soft gel or solid stick compositions containing a glycol or mixture of glycols and also containing a soap gelling agent. However, the gelling agent need not be a soap gelling agent, but can be, for example, other gelling agents known in the art.

The present invention is also directed to a clear cosmetic (for example, deodorant) gel composition, especially a soft gel or stick composition gelled utilizing a soap gelling agent, having reduced skin irritation potential yet having improved clarity.

Gel compositions, such as soap-gelled compositions, have proven to be a convenient and efficient vehicle for the application of various active ingredients to the skin. Such active ingredients include (but are not limited to) antiperspirants, deodorants, perfumes, sunscreens, cosmetics, emollients, insect repellants, medicaments and the like. Such gel compositions may be in the form of a soft gel and/or a stick. Rubbing a soft gel or solid stick composition containing an appropriate amount of active ingredient dissolved or dispersed therein against the skin causes transfer of a film of the composition to the skin surface against which the soft gel or stick is rubbed, leaving the active ingredient within the film of the composition on a desired skin surface area.

Conventional soap-gelled base formulations (that is, base gel compositions gelled using a soap gelling agent) for depositing the active ingredient normally include as major components a mixture of from about 3 to about 10% by weight, of the total weight of the composition, of an alkali metal salt of a fatty acid containing primarily 12 to 18 carbon atoms, e.g., sodium stearate or sodium palmitate soap, and a suitable solvent in which the soap is soluble, for example, water, organic solvents such as lower monohydric alcohols and/or glycols, or mixtures thereof. Soft gels or solid sticks may be formulated as known in the art, depending, for example, on amount of gelling agent utilized. For example, the stick is formed by pouring a mixture of the various components into a suitably shaped mold and permitting the composition to gel and cool, thereby hardening the composition.

A typical example of a water-based cosmetic stick formulation is disclosed in U.S. Pat. No. 4,322,400 to Yuhas, wherein the composition includes a mixture of water, sodium stearate, a cosmetically active ingredient and up to about 5% by weight, of the total weight of the composition, of sodium chloride, which tends to increase the setting point of the gel. The composition may also optionally contain up to about 10% by weight of one or more glycols, such as propylene glycol or polypropylene glycols having molecular weights of up to 25,000.

Other gel stick formulations, which are essentially free of water, are disclosed, for example, in U.S. Pat. No. 5,284,649 to Juneja. The composition of this patent includes a mixture of about 1–20% by weight, of the total weight of the composition, of a fatty acid soap, a zinc pyridinethione as a deodorant active, and about 7–95% by weight, of the total weight of the composition, of a polar solvent system which solubilizes the soap. Suitable solvents in the polar solvent system include lower monohydric alcohols such as ethanol or propanol, glycols such as ethylene glycol and propylene glycol, and polypropylene glycols such as dipropylene glycol, tripropylene glycol and higher glycols.

In addition, U.S. Pat. No. 4,504,465 to Sampson, et al discloses a water-free stick formulation based on a mixture of about 3–10% by weight soap, from about 6–70% by weight of an aliphatic polyhydric alcohol containing 2 or 3 carbon atoms and from 2 to 3 hydroxy groups, for example, ethylene glycol, propylene glycol, trimethylene glycol or glycerine, and from about 20 to 80% by weight of a condensation product of the formula $R(OC_3H_6)_a(OC_2H_4)_bOH$, wherein R is either hydrogen or a hydrocarbon chain having from about 2–20 carbon atoms and a and b are each from 0 to 35 and a+b is from 5 to 35. The preferred solvent system disclosed includes a mixture of a lower alkanol such as ethanol, propylene glycol and a major amount of polypropylene glycol, polyethylene glycol or condensates of propylene oxide with $C_2$–$C_{20}$ alcohols.

European Patent Application (EP) 284765 B1 discloses a soap-based cosmetic stick formulation of improved transparency and of more pleasing aesthetic appearance, wherein the solvent used to formulate the stick is dipropylene glycol or a mixture of dipropylene glycol and propylene glycol.

A non-soap-based stick antiperspirant formulation is disclosed in U.S. Pat. No. 5,200,174 to Gardlik, et al, wherein the solvent system includes a mixture of 2-oxazolidinone and one or more hydroxy solvents inclusive of lower alkanols, glycols such as propylene glycol and polyglycols such as polyethylene and polypropylene glycols. Dipropylene glycol and combinations of dipropylene glycol and propylene glycol are specifically used in the examples.

Gel stick formulations containing both a glycol and water are also known. For example, U.S. Pat. No. 4,702,916 to Geria discloses an analgesic stick composition including a mixture of from about 10–65% by weight of an alcohol, about 6–10% by weight soap and about 10–30% by weight water. The alcohol component preferably is propylene glycol.

One of the problems associated with the use of gel sticks, particularly soap-containing gel sticks, is that they may be harsh to the skin of some consumers, causing skin irritation and leading to the development of erythema. Substitution of the soap with other gelling agents such as dibenzylidene alditol as in U.S. Pat. No. 5,200,174, discussed above, may reduce the irritation problem, but these formulations present stability problems and add to the expense of the product.

Japanese Patent Document No. 63-270614 also discloses a soap-free gel base including a mixture of 0.1–5% by weight of a carboxyvinyl polymer used as a gelling agent, 30–80% by weight of a polyhydric alcohol and water. Examples of the disclosed polyhydric alcohols include propylene glycol, 1,3-butylene glycol, dipropylene glycol, tripropylene glycol and hexylene glycol. This composition is described as being safe to the skin.

A stick composition also disclosed as having a reduced tendency to irritate skin, while also being transparent, is disclosed in U.S. Pat. No. 5,128,123 to Brewster. This composition includes, in addition to soap and a polyhydric alcohol solvent such as propylene glycol, up to 40% by weight of an alkoxylate copolymer which is a condensate of ethylene oxide and propylene oxide, or an addition product condensate of ethylene oxide and propylene oxide with ethylene diamine.

The conventional wisdom up to now, for producing cosmetic formulations which are milder to the skin, appears to be (a) elimination of soap totally from the formulation and replacing it with a non-soap gelling agent, (b) reducing the amount of soap present in the formulation and including a different, less irritating costructurant such as alkylene oxide condensates, or (c) eliminating both the soap and irritating lower alcohols, such as ethanol, from the formulation.

Recently, in view of widespread consumer appeal, much effort has been expended for providing clear gel compositions, such as clear stick or soft gel compositions, which retain clarity over an extended period of time (that is, has a stable clarity) so as to have a long shelf life. A particular problem in gel compositions, for providing a clear composition, is avoiding crystals forming in the composition during, for example, the shelf life and until the product has been used up by the consumer.

The aforementioned U.S. Pat. No. 5,128,123 discloses cosmetic stick compositions which are not only milder but which are also clear, having the above-referred-to alkoxylate copolymer and, additionally, a basic amine clarifying agent; this patent further discloses that the clarifying agent is preferably selected from amino alkanols having from 2–6 hydroxyl groups, particularly effective being the propanol amines.

U.S. Pat. No. 5,128,123 also defines what is meant by the term "clear" with respect to the stick composition described therein. Specifically, the term "clear" has its usual dictionary definition; thus, a clear stick, like glass, allows for ready viewing of objects behind it. This patent contrasts clear sticks with translucent sticks, which allow light to pass through but causes the light to be so scattered that it will be impossible to clearly identify objects behind the translucent stick. This patent also shows that, in the present art, there is a difference between clear, translucent and opaque sticks; this patent goes on to define clear, translucent and opaque sticks based on transmittance of light of wavelengths in the range of 400 to 900 nm through a sample 1 cm thick.

U.S. patent application Ser. No. 08/054,302 to Kasat, et al, filed Apr. 30, 1993, the contents of which are incorporated herein by reference in their entirety, discloses that by incorporating a sodium salt of a methyl carboxy derivative of ethoxylated lauryl alcohol (for example, sodium laureth-13 carboxylate as defined in the CTFA International Cosmetic Ingredient Dictionary (4th Ed. 1991)) in a soap-gelled stick composition, a transparent, clear stick, which maintains such transparency and clarity for extended periods of time, can be achieved.

U.S. Pat. No. 5,424,070 to Kasat, et al, the contents of which are incorporated herein by reference in their entirety, discloses that by incorporating an Eumulgin compound (for example, Eumulgin L, which is PPG-2-Ceteareth-9, as defined in the aforementioned CTFA International Cosmetic Ingredient Dictionary) in a soap-gelled stick composition, a transparent, clear stick which maintains such transparency and clarity for extended periods of time can be achieved.

Neither of U.S. patent application Ser. No. 08/054,302 or U.S. Pat. No. 5,424,070 focus on reduction of skin irritation potential.

Notwithstanding the foregoing, it is still desired to provide a cosmetic gel composition, such as a deodorant gel composition, which can be in the form of a soft gel or hard stick, and which has reduced skin irritation potential. It is further desired to provide such composition, which is clear and which maintains such clarity over extended periods of time.

SUMMARY OF THE INVENTION

Accordingly, it is a first object of the present invention to provide a base gel composition for a cosmetic gel composition (that is, which can be used as a vehicle for applying a cosmetically active ingredient to the skin), having glycols incorporated therein, which has reduced skin irritation potential.

It is a further object of the present invention to provide a base gel composition, in which a cosmetically active ingredient can be incorporated to provide a cosmetic gel composition, having a soap gelling agent and glycols as a solvent therefor, and which has reduced skin irritation potential.

It is a further object of the present invention to provide a cosmetic gel composition having glycols and cosmetically active ingredients incorporated therein, having reduced skin irritation potential.

It is a still further object of the present invention to provide a cosmetic gel composition, gelled, for example, by a soap gelling agent, and having glycols and cosmetically active ingredients (for example, a deodorant active ingredient) incorporated therein, which has reduced skin irritation potential.

It is a still further object of the present invention to provide a soft gel or stick gel composition, containing glycols, which has reduced skin irritation potential.

It is a still further object of the present invention to provide a deodorant gel composition, especially in the form of a soft gel or stick, containing glycols, having reduced skin irritation potential.

It is a still further object of the present invention to provide a soap-gelled deodorant composition containing glycols, the composition being in the form of a soft gel or stick, having reduced skin irritation potential.

It is a still further object of the present invention to provide a translucent to clear soap-gelled cosmetic composition (for example, a translucent to clear soap-gelled deodorant composition), containing glycols, having reduced skin irritation potential.

The foregoing objectives are achieved through the present invention, which utilizes, as a glycol component of the base gel composition or cosmetic gel composition, at least one glycol corresponding to the formula $H(OC_3H_6)_nOH$, where n represents the number of repeating propylene oxide groups and ranges from 1 up to and including 80, with more than zero, and up to and including 100% by weight, of the total weight of the glycol component, having structure wherein n is 3 or 4; less than 20% by weight, of the total weight of the glycol component, having structure wherein n is 1; not more than 90% by weight, of the total weight of the glycol component, having structure wherein n is 2; and not more than 90% by weight, of the total weight of the glycol component, having structure wherein n is equal to or greater than 5. Thus, at least some of the glycol component must be tripropylene glycol and/or tetrapropylene glycol.

Desirably, at least 10% by weight, of the total weight of the glycol component, is tripropylene glycol and/or tetrapropylene glycol; and preferably 25–100% by weight, more preferably 50–100% by weight, of the total weight of the glycol component, is tripropylene glycol and/or tetrapropylene glycol.

The base gel composition according to the present invention can be in soft gel or stick form, and can contain a conventional soap gelling agent (but need not contain a conventional soap gelling agent; other known gelling agents can also be utilized). By utilizing the glycol component of the base gel composition as in the present invention, the composition is considerably less irritating to the skin than, e.g., conventional soap-based gel formulations.

The preferred glycols forming the glycol component of the gel composition of the present invention are tripropylene glycol and tetrapropylene glycol and mixtures thereof with dipropylene glycol and/or a polypropylene glycol where n in the above formula is 5 or greater. It is desired that at least 25% by weight, of the total weight of the glycol component, is tripropylene glycol; most preferably, the glycol component consists essentially of tripropylene glycol (for example, most preferably is 100% tripropylene glycol, with possibly other glycol (e.g., propylene glycol) impurities).

The most preferred compositions of the present invention are those where the glycol component contains less than 10% by weight, of the total weight of the glycol component, of propylene glycol; and, preferably, the compositions according to the present invention are essentially free of propylene glycol (for exampled containing only propylene glycol impurity introduced with the glycol component).

The base gel composition according to the present invention, which acts as a vehicle for depositing a cosmetically active ingredient on the skin, can also include water, as in conventional gel compositions.

As one aspect of the present invention, the composition according to the present invention utilizes a soap gelling agent, which includes a metal salt of at least one fatty acid having a chain length of about 12 to about 22 carbon atoms. By utilizing the glycol component of the present invention with such soap gelling agent, skin irritation due to the soap gelling agent can be reduced.

The cosmetically active ingredient incorporated in the base gel composition, according to the present invention, can be those conventionally known in the art, and include (but are not limited to) antiperspirant active agents, deodorant active agents, insect repellants, emollients, sunscreens, etc., as discussed previously and as described in U.S. Pat. No. 4,322,400, the contents of which are incorporation herein by reference in their entirety. By rubbing the cosmetic gel composition according to the present invention on the skin, the cosmetically active ingredient incorporated therein can be deposited in a film of the base gel composition on the skin, while achieving a film having reduced skin irritation potential.

Applicants have further found that by utilizing the glycol component according to the present invention, as discussed previously, in base gel compositions or cosmetic gel compositions, the compositions formed have reduced clarity. Having made this finding, applicants have also found, surprisingly, that by incorporating nonionic and/or anionic surface active agents in the composition, especially in soap-gelled compositions, clarity of the composition is significantly increased.

Accordingly, as an additional aspect of the present invention, applicants have found that by incorporating a surface active agent selected from the group consisting of anionic and nonionic surface active agents in the composition, as a clarifying agent, clarity of the composition is significantly increased, and a composition that is at least translucent (that is, that is translucent or clear) can be achieved.

Illustratively (but not limiting), anionic and nonionic surfactants, which can be utilized as clarifying agents according to this aspect of the present invention, include poloxamine 1307, PPG-2-Ceteareth-9 and sodium laureth-13 carboxylate. Illustratively (and not limiting), the surface active agent or mixture of surface active agents can be included in the composition in an amount of from about 3% to about 10% by weight, of the total weight of the composition.

Accordingly, by the present invention a base gel composition, including a base gel composition gelled utilizing a soap gelling agent, can be provided, having reduced skin irritation potential. A cosmetic gel composition containing the base gel composition and at least one cosmetically active ingredient (including cosmetic gel compositions gelled using a soap gelling agent), having reduced skin irritation potential, can be provided. Moreover, a composition that is at least translucent (i.e., that is translucent or clear), while containing polypropylene glycols, can be achieved.

DETAILED DESCRIPTION OF THE INVENTION

While the present invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Thus, while the description is most specific with respect to clear deodorant stick or soft gel compositions, the present invention is not limited to clear gel compositions, or to soft gel or stick compositions, or to deodorant compositions, but includes within its scope various cosmetic products, depending on the cosmetically active material incorporated in the composition.

Throughout the present disclosure, where compositions are described as including or comprising specific components or materials, it is contemplated by the inventors that compositions of the present invention also consist essentially of, or consist of, the recited components or materials. Accordingly, throughout the present disclosure any described composition of the present invention can consist essentially of, or consist of, the recited components or materials.

Throughout the present disclosure, various components of the disclosed compositions are denoted by their name in the CTFA International Cosmetic Ingredient Dictionary (4th Ed. 1991), the contents of which are incorporated herein by reference in their entirety.

The present invention, in one of its aspects, is directed to clear or translucent gel compositions. By clear or translucent, we mean the usual dictionary definitions of these terms. Thus, a clear gel composition, like glass, allows for ready viewing of objects behind it. A translucent gel composition, although allowing light to pass through, causes the light to be so scattered that it will be impossible to clearly identify objects behind the translucent gel. Opaque gels do not permit light to pass through. Thus, according to the present invention, there is a distinction between "clear" and "translucent" gels, and between these gels and "opaque" gels.

As mentioned previously, the present invention includes within its scope (but is not limited to) "soft gels" and sticks. The stick form can be distinguished from a soft gel in that, in a stick, the formulated product can maintain its shape for extended time periods outside the package, the product not losing its shape significantly (allowing for some shrinkage due to solvent evaporation). Soft gels can be suitably packaged in containers which have the appearance of a stick, but which dispense through apertures (for example, slots or pores) on the top surface of the package.

In the cosmetics field, systems are classified as soft gels or sticks, depending on their viscosity or hardness alone; typically, it is understood that soft gels are soft, deformable products while sticks are strictly free-standing solids. For example, by rheological analysis, a commercial deodorant stick has been determined to have a plateau storage modulus G' (w) of roughly $10^5$Pa and a complex viscosity of $10^6$Pa second, both at an angular frequency of 0.1 rad/sec). On the other hand, a commercial antiperspirant soft gel has been determined to have a G' (w) value of roughly $10^3$Pa and a complex viscosity of $10^4$Pa second (at 0.1 rad/sec).

As one aspect, the present invention contemplates a base gel composition, containing a glycol component, into which composition cosmetically active ingredients can be incorporated in order to provide a cosmetic gel composition, which is less irritating to the skin than conventional gel compositions. Such reduced irritation is achieved due to use of the specific glycol component forming part of the gel composition; that is, the glycol component corresponds to the formula $H(OC_3H_6)_nOH$, where n represents the number of repeating propylene oxide groups and ranges from 1 up to and including 80, (1) wherein more than zero, and up to and including 100% by weight, of the total weight of the glycol component having a structure wherein n is 3 or 4; (2) wherein less than 20% by weight, of the total weight of the glycol component, has structure wherein n is 1; (3) wherein not more than 90% by weight, of the total weight of the glycol component, has structure wherein n is 2; and (4) wherein not more than 90% by weight, of the total weight of the glycol component, has structure wherein n is equal to or greater than 5. Preferably, the glycol component contains not more than 40% by weight, more preferably not more than 20% by weight, of the total weight of the glycol component, of structure of the foregoing formula wherein n is 2. Desirably, the glycol component has not more than 20% by weight, of the total weight of the glycol component, of structure of the foregoing formula wherein n is at least 5.

Use of the present glycol component provides particularly good results in connection with soap-based compositions (for example, deodorant gel compositions gelled utilizing a soap gelling agent). It has long been known that soap-based deodorant gel compositions containing sufficient soap to form a suitable gel can cause skin irritation when applied to the skin of a person. Varying degrees of irritation have been observed whether or not the liquid used to formulate the soap-gelled composition is water or a conventional alcohol such as ethanol or a glycol such as propylene glycol, although water-based compositions show considerably less irritation. For this reason, it was believed that the primary skin irritant was the soap, and that irritation could not be eliminated by simply changing the liquid formulated with the soap. However, it has been surprisingly found that the use of liquids including tripropylene glycol or tetrapropylene glycol, and optionally higher molecular weight polypropylene glycols, as composition components, gives rise to significantly reduced irritation when such soap-gelled compositions are applied to the skin. Not only have such liquids themselves been found to be non-irritating, in contrast with liquids such as ethanol or propylene glycol, but they also appear to be less skin permeable themselves and also act to retard the permeation of soap (for example, sodium stearate as soap gelling agent) into the skin, thereby significantly reducing the skin irritation factor inherent with the use of these soaps.

The glycol content of the base gel composition may range as set forth previously, with preferred ranges set forth in Table 1. In Table 1, the "n" value of the glycol is the number of repeating propylene oxide groups in the aforementioned formula, and the percent is the percent by weight of the total glycol component.

TABLE 1

| n value of glycol | Preferred (% by wt) | More preferred (% by wt) | Most preferred (% by wt) |
| --- | --- | --- | --- |
| 3 or 4 | 10–100 | 25–100 | 35–100 |
| 2 | 0–40 | 0–35 | 0–35 |
| ≧5 | 0–90 | 0–35 | 0–25 |
| 1 | 0 to <20 | 0–10 | 0–5 |

Glycols used in the present invention where n averages 3 or 4 are tripropylene glycol (TPG) and tetrapropylene glycol (TetPG), respectively, with TPG being most preferred. Preferred glycols where n is greater than or equal to 5 include polypropylene glycols such as marketed by Dow Chemical under the trade designations P-425, P-1200, P-2000 and the like (the number represents the molecular weight approximation) or L-910 and L-1150. Where n is 2, the glycol is dipropylene glycol (DPG). Where n is 1, the glycol is propylene glycol (PG).

In the most preferred embodiments of the invention, the glycol component consists essentially of tripropylene glycol or includes mixtures of (1) tripropylene glycol with dipropylene glycol present at a respective mix ratio (weight) of 10:90 to 90:10; (2) mixtures of tripropylene glycol with a polypropylene glycol where n in the above formula is greater than or equal to 5, present at a respective mix (weight) ratio of 10:90 to 90:10; and (3) mixtures of all three of TPG, DPG and polypropylene glycol where n in the above formula is equal to or greater than 5, containing at least about 10% by weight of TPG, or preferably at least 35% or at least 50% by weight of TPG.

The most preferred compositions in these most preferred embodiments are those where TPG is present as at least 50% by weight of the glycol content.

In another preferred embodiment of this aspect of the present invention, the glycol component consists essentially of TetPG or includes mixtures of (1) TetPG with DPG present at a respective mix ratio by weight of 10:90 to 90:10; (2) mixtures of TetPG with a polypropylene glycol where n in the above formula is greater than or equal to 5, present at a respective mix (weight) ratio of 10:90 to 90:10; and (3) mixtures of all three of TetPG, DPG and polypropylene glycol where n in the above formula is equal to or greater than 5, containing at least about 10% by weight of TetPG, more preferably at least 35% and even more preferably at least 50% by weight of TetPG.

The most preferred compositions in these most preferred embodiments are those where TetPG is at least 50% by weight of the glycol content.

Since propylene glycol has been found to be a cause of skin erythema, it is preferred to keep the level of propylene glycol below 20% by weight, preferably below 10% by weight, more preferably below 5% by weight and most preferably at essentially 0, of the total glycol component. However, zero concentration of propylene glycol may be difficult to achieve, since propylene glycol may be present as an impurity in the polyglycols (e.g., in DPG and/or TPG). In any event, it is most preferred to have the propylene glycol in the composition at as low a level as possible.

In addition to the above glycols, the composition of this aspect of the present invention may also contain one or a mixture of other polyols which do not seriously contribute to skin irritation. For example, and not of a limiting nature, suitable polyols include glycerine and sorbitol.

The glycol component may constitute from about 10 to about 95% by weight, of the total weight of the gel composition, and most preferably constitutes at least about 60% by weight, of the total weight of the composition. At these levels, the glycol, either alone in the gel composition or when water is also included in the composition, can act as a solvent for the gelling agent (for example, the soap gelling agent), yet wherein the gelling agent can still gel therefrom, so as to form the gel composition.

As indicated previously, optionally the compositions according to the present invention can contain water. Water can be included in the composition in amounts up to 88% by weight; of the total weight of the composition. Preferably, where the compositions according to the present invention contain water, the water is included in the composition in an amount in a range from about 5% by weight, to about 88% by weight, water, of the total weight of the composition. Preferred water-containing compositions contain from about 5% to about 40% by weight water, more preferably from about 10% to 30% by weight water, of the total weight of the composition. The water serves as a diluent for the glycol and polyol components and may assist in solubilization of actives or other ingredients added to the compositions, as well as assist in gelation of the composition and in formation of a more transparent gel.

The gel-forming agent used in the present invention can be one of those conventionally used in the art. A preferred gel-forming agent, appropriate in deodorant gel compositions, is a soap which is a metal salt of one or more fatty acids having a chain length of 12–22 carbon atoms. Preferred are the alkali metal, e.g., sodium or potassium, salts of fatty acids containing 12–22 carbon atoms. The fatty acid portion of the soap is preferably a relatively pure saturated or unsaturated $C_{12}$ to $C_{22}$ acid including myristic, palmitic, stearic, oleic, linoleic, linolenic and margaric acids, as well as mixtures thereof. Naturally occurring sources of such acids include coconut oil, beef tallow, lanolin, fish oil, palm oil, peanut oil and the like.

Thus, preferred soaps include sodium stearate, sodium palmitate, potassium stearate, potassium palmitate, potassium myristate and sodium myristate, with sodium stearate being most preferred. Generally, the sodium soaps are used to formulate sticks, with stick hardness being directly proportional to the level of sodium stearate. The potassium soaps may be used to form soft gels.

The most preferred soap is sodium stearate, which in actuality is a mixture of sodium salts of fatty acids have $C_{12}$ to $C_{22}$ carbon chain lengths in various ratios. As for various soap gelling agents which can be utilized according to the present invention, see U.S. Pat. No. 5,424,070, the contents of which have previously been incorporated herein by reference.

The soap may be present in the composition at a level of from about 2–12% by weight, more preferably 3–10% by weight, most preferably from about 5–9% by weight, of the total weight of the composition.

Various active ingredients can be incorporated in the base gel composition in order to form the cosmetic gel composition of the present invention. Thus, depending on the end use, any one of, e.g., deodorant, insecticide, sunscreen, emollient, antiperspirant, etc., active ingredients can be incorporated in the composition, so as to form a cosmetic gel composition that has deodorancy properties, insecticide properties, sunscreen properties, emollient properties, antiperspirant properties, etc. The active ingredients can include biologically active materials such as antibacterials or bacteriostats, as well as fungicides, analgesics, emollients, ultraviolet absorbers or sunscreens, talc, etc.

The active ingredient must be stable in the environment of the gel composition. For example, where the gelling agent is a soap such as sodium stearate, any active ingredient must be stable in the alkali environment provided by the sodium stearate/glycol or sodium stearate/water/glycol vehicle.

Various active ingredients which can be incorporated in the cosmetic gel compositions according to this aspect of the present invention are disclosed in U.S. Pat. No. 4,322,400, the contents of which are incorporated herein by reference in their entirety. Other active ingredients are disclosed in U.S. Pat. No. 4,382,079 to Marschner, the contents of which are also incorporated herein by reference in their entirety. Depending on identity and function, the actives may be added to the gel compositions at various levels, i.e., in sufficient amounts to achieve the desired effect; for example, deodorant actives may be added to soap-based gel compositions at levels up to about 3% by weight of the active ingredient, of the total weight of the composition. Preferably, these deodorant actives are added in a range of from about 0.01 to about 2% by weight, more preferably from about 0.05 to about 0.75% by weight, of the total weight of the composition.

Where a deodorant active ingredient is added as the cosmetically active ingredient, the composition can be used as a deodorant gel composition. A preferred category of deodorant active ingredients are the antibacterials, and the one most preferred in deodorant soap-based gel compositions according to the present invention is 2-4-4'-trichloro-2'-hydroxy diphenyl ether (Triclosan). Other antibacterial ingredients include bacteriostatic quaternary ammonium compounds such as cetyl trimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-myristoyl glycine, potassium N-lauroyl sarcosine and stearyl trimethyl ammonium chloride. The antibacterial or bacteriostatic compounds are usually present in a range of about 0.05% to 1.0% by weight, of the total weight of the composition; preferably, 0.05%–0.5% by weight of the antibacterial or bacteriostatic compound is present.

Conventional deodorant active materials, for forming deodorant gel compositions (including deodorant gel compositions containing soap gelling agents) according to this aspect of the present invention, are disclosed in previously mentioned U.S. Pat. No. 4,322,400 and in U.S. Pat. No. 4,759,924 to Luebbe, et al. These deodorant active materials include known deoperfumes.

Various additional components, such as coloring agents, including dyes and pigments, fillers, fragrances, etc., can be incorporated in the gel compositions of this aspect of the present invention. Fragrances and coloring agents are those which previously have conventionally been incorporated in cosmetic sticks. Reference is made, for example, to U.S. Pat. No 5,114,717 to Kuznitz, et al; and U.S. Pat. No. 5,380,707 to Barr, et al, the contents of each of which are incorporated herein by reference in their entirety, for various fragrance compounds which have been incorporated in cosmetic stick compositions. This invention is not limited to use of such fragrance compounds, but can include fragrance compounds conventionally in use, either for clear or non-clear sticks.

When these additional components are present, they, illustratively, are included in the composition in amounts ranging from between about 0.1% to about 3.0% by weight, of the total weight of the composition.

Various other optional components can be included in the compositions according to the present invention. For example, in addition to the glycol components, water and soap gelling agents, and, for example, in addition to the deodorant active ingredient (where the composition is a deodorant gel composition), the compositions can also include emollients, fillers, chelating agents (for example, ethylene diamine tetraacetic acid), lauramide DEA, antioxidants (e.g., sodium metabisulphite), pH regulating agents and other solubilizers as conventionally known in gel formulations.

Other optional components conventionally incorporated in soap-based gels are disclosed in U.S. Pat. No 4,504,465, the contents of which are incorporated herein by reference in their entirety.

An illustrative deodorant gel composition within the scope of this aspect of the present invention is set forth in the following. This composition is one example, and is not limiting of the present invention. The composition includes, in percent by weight of the total weight of the composition:

(a) 2%–12% by weight of a gelling agent;

(b) 10%–95% by weight of a glycol component, the glycol component having a mixture of glycols of the formula $H(OC_3H_6)_nOH$, n being as defined previously, with the provisos set forth previously;

(c) deodorant active ingredients, in an amount sufficient to have a deodorizing effect; and (d) 0–88% by weight water.

Preferred amounts and embodiments of the glycol component are as discussed previously.

A more specific illustration of a deodorant gel composition of the present invention, which is not intended to be limiting of the present invention, is set forth in the following, in percent by weight of the total weight of the composition:

(a) 3%–10% of a soap that includes metal salts of at least one fatty acid having carbon chain length in the range of 12–22 carbon atoms;

(b) 0–20% by weight propylene glycol;

(c) 40%–80% by weight polypropylene glycol having a formula $H(OC_3H_6)_nOH$, where n ranges from 2 up to and including 80, no more than 35% by weight of the polypropylene glycol has n=2, and no more than 20% by weight of the polypropylene glycol has $n \geq 5$;

(d) 0–0.5% by weight Triclosan; and (e) 0–2.5% by weight fragrance and color.

As another aspect of the present invention, applicants have found that replacement of propylene glycol in, e.g., a deodorant stick composition with tripropylene glycol or higher molecular weight polypropylene glycols, significantly reduces skin irritation, but leads to a reduction in clarity of the composition. Having discovered this problem in connection with clarity, applicants have also found that incorporation of nonionic and/or anionic surface active agents into the composition containing TPG and/or higher molecular weight polypropylene glycols, significantly increases clarity. By incorporating sufficient amounts of the surface active agents in the composition, a translucent, or even a clear, deodorant stick composition can be achieved.

Specific illustrative surface active agents which can be incorporated as clarifying agents according to this aspect of the present invention include poloxamine 1307, PPG-2-Ceteareth-9 and sodium laureth-13-carboxylate. However, the nonionic and/or anionic surface active agents which can be utilized as a clarifying agent according to the present invention are not limited to the above-referred-to three surfactants. Various other known nonionic and/or anionic surface active agents can be utilized.

The nonionic and/or anionic surface active agent is included in the composition in an amount sufficient to improve clarity of the composition. Illustratively, and not limiting, this surface active agent (or mixture of surface active agents) is incorporated in the composition in an amount of about 3% to about 10% by weight, of the total weight of the composition.

Compositions according to the present invention can be made utilizing conventional techniques for forming gel compositions. For example, for preparing stick compositions according to the present invention, the components, in liquid (molten) form, can be mixed together and then poured into dispensing packages or molds, after which they are permitted to gel. Heating of the components to 60°–90° C. is usually necessary in order to provide the components in liquid form for the necessary mixing. In view of processing at relatively high temperatures, it is desirable to add the fragrances at a relatively late time during mixing, as is conventional in the art, so as to avoid volatilization of the fragrances.

The gels according to the present invention are used as such products are conventionally used by the consumer. Thus, the soft gel or the stick is rubbed, for example, on the area of the body where application is desired. Illustratively, in the case of a deodorant soft gel or stick for application to the axillary area, the soft gel or stick is rubbed in the axillary area to deposit the deodorant active agent on the skin. In use the end of the stick is exposed from the conventional dispensing package and may, after use, be retracted back into the dispensing container until the next use.

In the case of a soft gel, the consumer extrudes an appropriate amount of gel from the package through slots or pores in the top of the package and applies the dispensed amount by rubbing the top of the package on the skin.

In the following, specific examples within the scope of the various aspects of the present invention will be set forth. The stated percentages are percentages by weight, of the stated component, relative to the total weight of the composition. The names utilized are the CTFA names for the ingredients, where applicable.

EXAMPLES 1–8

A series of deodorant stick formulations were prepared having the following general composition:

| Component | % by weight |
| --- | --- |
| Glycol | 70.25 |
| Deionized water | 21.50 |
| Sodium stearate | 7.0 |
| Perfume | 1.0 |
| Triclosan | 0.25 |
| Dye | 0.0005 |

The compositions were prepared by mixing all the ingredients except the perfume at elevated temperatures sufficient to form a liquid solution or suspension, adding the perfume and cooling.

The particular glycols employed for the glycol component in the respective formulations of Examples 1–8, and amounts thereof in percent by weight of the total formulation weight, are shown in the following Table 2. The glycols identified in Table 2 are as follows: PG is propylene glycol; DPG is dipropylene glycol; TPG is tripropylene glycol; and PPG is polypropylene glycol (MW about 425).

TABLE 2

| Example | PG | DPG | TPG | PPG |
| --- | --- | --- | --- | --- |
| 1 | 70.25 | — | — | — |
| 2 | 0.02 | 70.2 | — | — |
| 3 | 0.02 | — | 70.2 | — |
| 4 | 0.02 | 35.1 | 35.1 | — |
| 5 | 0.02 | 25.1 | 25.1 | 20 |
| 6 | 17.6 | — | 52.7 | — |
| 7 | 35.2 | — | — | 35.1 |
| 8 | 20.2 | 25 | 25 | — |

Each of the formulations of Examples 1–8 was evaluated for their tendency to cause skin erythema using the following protocol. In accordance with the protocol, female panelist volunteers between the ages of 18 and 55 were selected based on a medical questionnaire and medical evaluation which excluded panelists who were pregnant, breast feeding, reported known allergies to cosmetics, were taking prescription medications or who showed signs of systematic or cutaneous diseases, except for facial acne, or the presence of forearm irritation. The testing was carried out using Hill Top Chambers, which are small circular plastic cups about 1.5 cm in diameter and about 2–3 mm high and contain a non-woven cotton pad.

Test products in the form of a gel were heated in a sealed vial in a microwave to a temperature sufficient to form a liquid, after which about 0.3 mL of each test product was applied to the cotton pad of a different designated chamber. Each chamber was then covered to prevent evaporation and allowed to equilibrate to room temperature for 30 minutes.

Each product to be tested was coded after which each chamber was applied (cotton side in) with the volar forearms of each test panelist in a random or round-robin distribution. Each chamber was covered with medical tape to maintain an occluded environment. After 24 hours, the chambers were removed from each panelist and the forearms were rinsed, but not scrubbed, with running water and patted dry.

After 3 hours equilibration time, the degree of erythema for each test site was evaluated visually by a trained evaluator, as described below. Panelists were then re-patched with fresh test solutions on the same test sites for an additional 24 hours, after which the patches were removed and erythema once again evaluated as described above. In most tests, the sites were re-scored after having been left uncovered for an additional 24 hours. Sites with an erythema score of greater than 2 after removal of the first chamber were not re-patched and were assigned a score of 4 after the second 24 hour patch period. Data generated by the test protocol was analyzed by a non-parametric Friedman analysis to detect statistically significant differences at the 5% confidence level.

Baseline values of erythema were recorded for each test panelist based on the following 0–4 scale:

| Measurement | Scale | Observation |
| --- | --- | --- |
| Erythema | 0 | No redness |
|  | 1 | Slight redness, spotty and diffuse |
|  | 2 | Moderate, uniform redness |
|  | 3 | Intense redness |
|  | 4 | Fiery red |

Control samples comprising 5% by weight aqueous solutions of commercial "Ivory" and "Dove" soaps were also included in the tests where indicated, to show relative values as compared with harsher and milder soaps.

The following test results shown in Table 3 were obtained in a first test protocol.

TABLE 3

| Control and Example Nos. | 24 Hour Patch Mean Erythema | Statistics I Group (P ≦ 0.05) | 48 Hour Patch Mean Erythema | Statistics I Group (P ≦ 0.05) | Post Patch Mean Erythema | Statistics I Group (P ≦ 0.05) |
| --- | --- | --- | --- | --- | --- | --- |
| 5% Ivory | 1.48 | A | 1.80 | A | 1.32 | A |
| 1. PG | 1.08 | A | 1.28 | A | 0.84 | B |
| 5% Dove | 0.56 | B | 0.96 | B | 0.96 | B |
| 2. DPG | 0.20 | C, D | 0.36 | C | 0.24 | D |
| 3. TPG | 0.08 | D | 0.04 | D | 0.00 | E |

This test data in Table 3 demonstrates that the formulations containing DPG and TPG as the sole glycols are considerably less irritating to the skin than Example 1 containing propylene glycol (PG) as the sole glycol, and also less irritating than the commercial controls. Example 3 containing TPG as the sole glycol component is less irritating than Example 2 containing DPG as the sole glycol.

In a second test protocol, results as indicated in Table 4 were achieved.

TABLE 4

| Control and Example Nos. | 24 Hour Patch Mean Erythema | Statistics I Group (P = 0.05) | 48 Hour Patch Mean Erythema | Statistics I Group (P ≦ 0.05) | Post Patch Mean Erythema | Statistics I Group (P ≦ 0.05) |
|---|---|---|---|---|---|---|
| 1. PG | 1.13 | A | 1.22 | B | 1.13 | A |
| 5% Dove | 0.52 | B | 0.89 | C, D | 1.15 | A |
| 8. PG + DPG + TPG | 0.57 | B | 1.04 | B, C | 1.11 | A |
| 5. DPG + TPG + PPG | 0.11 | C | 0.35 | E | 0.46 | B |

The series of data in Table 4 demonstrate that Example 5 containing a mixture of DPG (25), TPG (25) and PPG 425 (20) is considerably less irritating than Example 1 containing propylene glycol as the sole glycol and even less irritating in this test than the "Dove" control. The results achieved for Example 8, which is a mixture of PG (20), DPG (25) and TPG (25) indicates that the presence of 20% by weight of propylene glycol in the product serves to increase the irritation factor as compared with Example 5 which contains PPG instead of PG.

In a third test protocol, results as indicated in Table 5 were achieved.

TABLE 5

| Control and Example Nos. | 24 Hour Patch Mean Erythema | Statistics I Group (P≦0.05) | 48 Hour Patch Mean Erythema | Statistics I Group (P≦0.05) |
|---|---|---|---|---|
| 5% Ivory | 1.20 | A | 2.20 | A |
| 5% Dove | 0.75 | A, B | 1.00 | B, C |
| 1. PG | 0.60 | B, C | 1.25 | B |
| 7. PG + PPG | 0.20 | C, D | 0.80 | C, D |
| 6. PG + TPG | 0.20 | C, D | 0.60 | C, D, E |
| 2. DPG | 0.20 | C, D | 0.55 | D, E, F |
| 4. DPG + TPG | 0.00 | D | 0.20 | E, F |
| 3. TPG | 0.00 | D | 0.10 | F |

This test data in Table 5 demonstrates that Example 4 containing equal parts by weight of DPG and TPG and Example 3 containing TPG as the sole glycol component are essentially non-irritating to the skin. Examples 6 and 7 wherein a portion of the PG is replaced with TPG and PPG are less irritating than Example 1 which contains PG as the sole glycol component, but are more irritating than Examples 3 and 4.

From this data it is evident that not only is PG a major contributor to irritation caused by underarm deodorant products, but that compositions containing TPG as the sole glycol component or mixtures of TPG with one or more of DPG and PPG are considerably less irritating to the skin than compositions containing PG as the sole glycol or compositions containing significant amounts of PG mixed with other glycols.

Surprisingly, it has also been found that the high molecular weight glycols of the present invention appear to minimize irritation caused by the other components of standard underarm deodorant products, such as soap and fragrances.

| Component | % by weight, of the total weight of the composition | | | |
|---|---|---|---|---|
| | 9 | 10 | 11 | 12 |
| Propylene Glycol | | | | |
| Dipropylene Glycol | 35.5 | 35.5 | 35.5 | |
| Tripropylene Glycol | 35.5 | 35.5 | 35.5 | 73.25 |
| Triclosan | 0.25 | 0.25 | 0.25 | 0.25 |
| Sodium Stearate | 7.0 | 7.0 | 7.0 | 6.0 |
| Color Solution | 0.08 | 0.08 | 0.08 | 0.08 |
| Fragrance | 1.0 | 1.0 | 1.0 | 1.0 |
| Sodium Chloride | | | | |
| Poloxamine 1307 | 4.0 | | | 4.0 |
| PPG-2-Ceteareth-9 | | 3.0 | | |
| Sodium Laureth-13-Carboxylate | | | 6.0 | |
| Water | QS | QS | QS | QS |

The compositions as in Examples 9–12 were produced using processing as discussed above in connection with Examples 1–8. These Examples 9–12 include a surface active agent that acts as a clarifying agent in the present compositions, the compositions having significantly increased clarity as compared to compositions containing the polypropylene glycols but without the clarifying agent.

Accordingly, through use of the present invention, a cosmetic gel composition (such as a soft gel or stick), including deodorant gel compositions gelled utilizing a soap gelling agent, having reduced skin irritation potential, can be achieved. Moreover, such composition having reduced skin irritation potential, yet which is at least translucent (and, in some instances, is clear) can be achieved.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A base gel composition exhibiting reduced skin irritation comprising:
   (a) a gelling agent comprising 3%–10% of a soap comprising metal salts of at least one fatty acid having a carbon chain length of 12 to 22 carbon atoms; and
   (b) a glycol component in which:
   (i) each glycol used to form the glycol component has a formula of $H(OC_3H_6)_nOH$, where n represents the number of repeating propylene oxide groups and ranges from 2 up to and including 80 provided that:
   (1) not more than 35% by weight of the polypropylene glycol has n=2, and (2) not more than 20% by weight of the polypropylene glycol has n greater than or equal to 5;

(ii) 10–100% by weight of the glycol component is selected from the group consisting of tripropylene glycol, tetrapropylene glycol and mixtures thereof; and (iii) the base gel composition comprises less than 20% by weight based on the total weight of the composition of propylene glycol.

2. The base gel composition according to claim 1, wherein the at least one glycol comprises less than 10% by weight, of the total weight of the composition, of propylene glycol.

3. The base gel composition according to claim 1, which is free of added propylene glycol.

4. The base gel composition according to claim 1, further comprising at least one surface active agent, selected from the group consisting of anionic surface active agents and nonionic surface active agents, that acts as a clarifying agent for the composition, the surface active agent being incorporated in the composition in an amount such that the composition is translucent or clear.

5. The base gel composition according to claim 4 wherein the at least one surface active agent is selected from the group consisting of a polyoxyethylene, polyoxypropylene block polymer of ethylene diamine that conforms to the formula

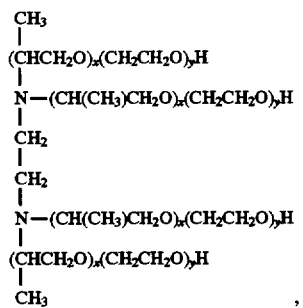

in which x=23 and y=74: a polyoxypropylene, polyoxyethylene ether of cetearyl alcohol having formula R(OCH(CH₃)CH₂)ₐ(OCH₂CH₂)ᵦOH, where R is a blend of cetyl and stearyl radicals, a has an average value of 2 and b has an average value of 9; and a sodium salt of the carboxylic acid derived from laureth-13 having formula CH₃(CH₂)₁₀CH₂(OCH₂CH₂)₁₂OCH₂COONa.

6. A cosmetic gel composition comprising the base gel composition according to claim 1 and at least one cosmetically active ingredient, the at least one cosmetically active ingredient being included in the cosmetic gel composition in an amount so as to have a cosmetic effect.

7. The cosmetic gel composition according to claim 1, wherein said soap comprises sodium stearate.

8. The cosmetic gel composition according to claim 7, wherein the cosmetically active ingredient comprises a deodorant active agent, in an amount sufficient to have a deodorizing effect, whereby a deodorant gel composition is provided.

9. The deodorant gel composition according to claim 8, wherein the deodorant active agent comprises an antibacterial agent.

10. The deodorant gel composition according to claim 9, wherein said antibacterial agent is 2-4-4'-trichloro-2'-hydroxy diphenyl ether.

11. The deodorant gel composition according to claim 9, wherein said antibacterial agent is a bacteriostatic quaternary ammonium compound.

12. The deodorant gel composition according to claim 9, wherein the deodorant active agent comprises a fragrance.

13. The deodorant gel composition according to claim 8, wherein the deodorant gel composition further comprises at least one surface active agent, selected from the group consisting of anionic surface active agents and nonionic surface active agents, that acts as a clarifying agent for the deodorant gel composition, the surface active agent being incorporated in the deodorant gel composition in an amount such that the deodorant gel composition is translucent or clear.

14. The deodorant gel composition according to claim 13 wherein the at least one surface active agent is selected from the group consisting of a polyoxyethylene, polyoxypropylene block polymer of ethylene diamine that conforms to the formula

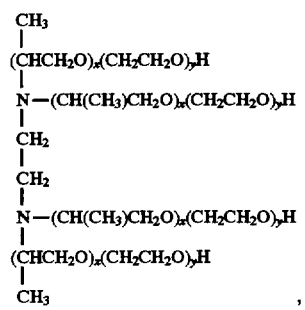

in which x=23 and y=74; a polyoxypropylene, polyoxyethylene ether of cetearyl alcohol having formula R(OCH(CH₃)CH₂)ₐ(OCH₂CH₂)ᵦOH, where R is a blend of cetyl and stearyl radicals, a has an average value of 2 and b has an average value of 9; and a sodium salt of the carboxylic acid derived from laureth-13 having formula CH₃(CH₂)₁₀CH₂(OCH₂CH₂)₁₂OCH₂COONa.

15. The deodorant gel composition according to claim 13, wherein the at least one surface active agent is added in the deodorant gel composition in an amount of about 3% to about 10% by weight, of the total weight of the deodorant gel composition.

16. The cosmetic gel composition according to claim 6, wherein the cosmetic gel composition is a soft gel.

17. The cosmetic gel composition according to claim 6, wherein the cosmetic gel composition is a stick composition.

18. A deodorant gel composition comprising in percent by weight of the total weight of the composition:

(a) a base gel composition according to claim 45;

(b) a deodorant active ingredient in an amount sufficient to have a deodorizing effect; and (c) 0–88% water.

19. The deodorant gel composition according to claim 18, further comprising a clarifying agent selected from the group consisting of nonionic and anionic surface active agents, the clarifying agent being included in the composition in an amount so as to provide a translucent or clear composition.

20. The deodorant gel composition according to claim 18, wherein the at least one glycol is substantially free of added propylene glycol.

21. The deodorant gel composition according to claim 18, wherein the composition is a stick composition.

22. The base gel composition according to claim 1 in which n=3, n=4, or the glycol component is a mixture of glycols where n=3 and 4.

23. The base gel composition of claim 1 in which more than one glycol is present and at least 10 percent by weight of the total weight of the glycol component is selected from the group consisting of tripropylene glycol, tetrapropylene glycol and mixtures thereof.

24. The base gel composition of claim 1 in which 25%–100% of the total weight of the glycol component is selected from the group consisting of tripropylene glycol, tetrapropylene glycol and mixtures thereof.

25. The base gel composition of claim 1 in which 50%–100% of the total weight of the glycol component is selected from the group consisting of tripropylene glycol, tetrapropylene glycol and mixtures thereof.

26. A deodorant gel composition comprising in percent by weight of the total weight of the composition:
   (a) 3%–10% of a soap comprising metal salts of at least one fatty acid having a carbon chain length of 12 to 22 carbon atoms;
   (b) 0 to less than 20% by weight propylene glycol;
   (c) 40%–80% by weight polypropylene glycol having a formula $H(OC_3H_6)_nOH$ where n is a number from 2–80, provided that:
      (i) not more than 35% by weight of the polypropylene glycol has n=2, and
      (ii) not more than 20% by weight of the polypropylene glycol has $n \geq 5$;
   (d) 0–0.5% by weight 2-4-4'-trichloro-2'-hydroxydiphenyl ether; and
   (e) 0–2.5% by weight fragrance and color.

27. The deodorant gel composition according to claim 26, wherein said metal salts of at least one fatty acid are sodium salts of at least one fatty acid.

28. The deodorant gel composition according to claim 26, further comprising at least one surface active agent selected from the group consisting of anionic and nonionic surface active agents, as a clarifying agent in the composition, the at least one surface active agent being incorporated in the composition in an amount sufficient to provide a translucent or a clear deodorant gel composition.

29. The deodorant gel composition according to claim 28, wherein the composition comprises from about 3% to about 10% by weight, of the total weight of the composition, of the surface active agent.

* * * * *